United States Patent

Schmid et al.

[11] Patent Number: 6,037,427
[45] Date of Patent: Mar. 14, 2000

[54] POLYMERIZATION WITH SUBSTITUTED INDENYL CYCLOPENTADIENYL METALLOCENES

[76] Inventors: Claudia Schmid, Wolfsbacher Str. 30, D-95448; Helmut G. Alt, Wacholderweg 27, D-95445, both of Bayreuth, Germany; M. Bruce Welch, 4750 Lewis Dr., Bartlesville, Okla. 74006

[21] Appl. No.: 09/035,985

[22] Filed: Mar. 6, 1998

Related U.S. Application Data

[62] Division of application No. 08/622,907, Mar. 29, 1996, Pat. No. 5,780,659.

[51] Int. Cl.⁷ .......................... C08F 4/44; C08F 110/06; C08F 110/02; B01J 31/00; B01J 37/00
[52] U.S. Cl. ........................ 526/127; 526/64; 526/160; 526/351; 526/352; 526/943; 502/103; 502/117
[58] Field of Search ............. 526/64, 127, 160, 526/351, 352, 943; 502/103, 117

[56] References Cited

U.S. PATENT DOCUMENTS

| | | | |
|---|---|---|---|
| 5,049,535 | 9/1991 | Resconi et al. | 502/117 |
| 5,084,534 | 1/1992 | Welborn, Jr. et al. | 526/160 |
| 5,126,303 | 6/1992 | Resconi et al. | 502/117 |
| 5,223,467 | 6/1993 | Razavi | 502/152 |
| 5,225,092 | 7/1993 | Emert et al. | 252/50 |
| 5,304,622 | 4/1994 | Ikai et al. | 528/16 |
| 5,331,054 | 7/1994 | Fujita et al. | 525/240 |
| 5,498,581 | 3/1996 | Welch et al. | 556/53 |
| 5,543,373 | 8/1996 | Winter et al. | 556/52 |
| 5,594,080 | 1/1997 | Waymouth et al. | 526/126 |
| 5,646,322 | 7/1997 | Van Beek et al. | 556/11 |
| 5,780,659 | 7/1998 | Schmid et al. | 556/11 |

FOREIGN PATENT DOCUMENTS

| | | |
|---|---|---|
| 0 685 495 | 12/1995 | European Pat. Off. . |
| WO 94/11406 | 5/1994 | WIPO . |

OTHER PUBLICATIONS

Chem. Abstr., vol. 125, No. 20, Nov. 11, 1996, abstract 248570z.
Polym. Prep. (ACS, Div. Polym. Chem.) 1996, vol. 37(c), p. 475, R.L. Kravchenko et al.
E. Samuel et al., JACS, vol. 95, No. 19, pp. 6263–6267, Sep. 1973.

*Primary Examiner*—Mark L. Bell
*Assistant Examiner*—J. Pasterczyk
*Attorney, Agent, or Firm*—Edward L. Bowan

[57] ABSTRACT

Olefins are polymerized with a catalyst system resulting from the combination of unbridged substituted indenyl cyclopentadienyl metallocenes and an organoaluminum cocatalyst.

19 Claims, No Drawings

POLYMERIZATION WITH SUBSTITUTED INDENYL CYCLOPENTADIENYL METALLOCENES

This application is a Division of application Ser. No. 08/622,907, filed Mar. 24, 1996 now U.S. Pat. No. 5,780,659, the disclosure of which is incorporated herein by reference.

This invention relates to metallocenes. In another aspect this invention relates to catalyst systems useful for the polymerization or olefins. In another aspect this invention relates to methods for polymerizing olefins using specific types of metallocenes which can be referred to as unbridged metallocene of a substituted indenyl and cyclopentadienyl.

BACKGROUND OF THE INVENTION

Since the discovery of ferrocene in 1951, a number of metallocenes have been prepared by the combination of compounds prepared from cyclopentadiene-type compounds and various transition metals. The term "cyclopentadiene-type compounds" as used herein refers to compounds containing the cyclopentadiene structure. Examples include unsubstituted cyclopentadiene, unsubstituted indene, unsubstituted fluorene, and substituted varieties of such compounds. Also included is tetrahydroindene.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and location of substitutions on cyclopentadienyl-type ligands has been found to affect the activity of the catalyst, the stereoselectivity of the catalyst, the stability of the catalyst, or various properties of the resulting polymer; however, the effects of various substituents is still largely an empirical matter, that is, experiments must be conducted in order to determine just what effect a particular variation in the chemical structure of the metallocene will have upon its behavior as a polymerization catalyst.

While there are references in the prior art which contain broad general formulas that encompass a vast number of unbridged metallocenes, it is considered unlikely that all of the metallocenes within the broad disclosures of publications have actually been prepared and evaluated for their polymerization effects. For example, while U.S. Pat. Nos. 5,049,535; 5,225,092; and 5,126,303 and WO 94/11406 contain allegations regarding a wide range of both bridged and unbridged metallocenes, the only actual examples of unbridged metallocenes are those in which two identical cyclopentadienyl-type ligands are present, i.e. symmetrical unbridged metallocenes. Similarly, while U.S. Pat. No. 5,331,054 names two unsymmetrical unbridged metallocenes, viz. (cyclopentadienyl) (indenyl) and (cyclopentadienyl) (fluorenyl) zirconium dichlorides, those compounds do not contain substituted indenyl groups and again the actual examples used symmetrical unbridged metallocenes. While published EPC application 685,485 discloses unsymmetrical unbridged metallocenes containing substituted indenyl groups, the metallocenes also contain a pentamethylcyclopentadienyl group. Similarly, while U.S. Pat. No. 5,223,467 proposes unsymmetrical unbridged metallocenes which could include substituted indenyl groups it also specifies that the other cyclopentadienyl ring also be substituted and it does not contain any actual examples having an indenyl ligand.

Many of the unbridged metallocenes have been found not to be sufficiently active in the polymerization of olefins to be of significant commercial interest. The aforementioned EPC 685,485 reveals that indenyl pentamethylcyclopentadienyl Zr dichloride is much more active than indenyl cyclopentadienyl, which in turn is much more active than either the bis indenyl or bis cyclopentadienyl counterparts. Prior to the present applicants' work there does not appear to have been any work which suggests what effect substituents on indenyl would have on an unsymmetrical unbridged (indenyl) (unsubstituted cyclopentadienyl) metallocene.

An object of the present invention is to provide certain new substituted indenyl-containing metallocenes. Still another object of the present invention is to provide polymerization catalyst systems employing the specific indenyl-type metallocenes. Still yet another object of the present invention is to provide processes for the polymerization of olefins using specific indenyl-type metallocene catalyst systems. Yet another object of the present invention is to provide catalyst systems which provide unusually high activity or molecular weight in the polymerization of olefins.

SUMMARY OF THE INVENTION

In accordance with the present invention, there are provided new unbridged substituted metallocenes of the formula $(In)(Cp)MQ_2$ wherein In is a substituted indenyl radical having a substituent in at least one of the 1, 2, and 3 positions, said substituents being selected from hydrocarbyl radicals having 1 to 10 carbon atoms, more preferably 1 to 6 carbon atoms, and trialkylsilyl radicals wherein the alkyl groups have 1 to 4 carbons; Cp is an unsubstituted cyclopentadienyl radical; M is a transition metal selected from the group consisting of titanium, zirconium, and hafnium; and each Q is the same or different and is selected from the group consisting of hydrocarbyl radicals having 1 to 12 carbon atoms, alkoxy radicals having 1 to 12 carbon atoms, aryloxy radicals having 6 to 12 carbon atoms, hydrogen, and halides.

In accordance with another aspect of the present invention, there is provided a catalyst system comprising the specific types of unbridged indenyl-containing metallocenes as described above in combination with a suitable cocatalyst.

In accordance with still another aspect ofthe present invention, there is provided a process for the polymerization of olefins comprising contacting said olefins under suitable reaction conditions with a catalyst system comprising an indenyl-containing metallocene as described above in combination with a suitable cocatalyst.

DETAILED DESCRIPTION OF THE INVENTION

The novel metallocenes provided in accordance with the present invention are unbridged, that is the indenyl ligand and the cyclopentadienyl ligand that are bound to the metal are not bound to each other. In this disclosure the substituent locations are numbered in accordance with the IUPAC Nomenclature of Organic Chemistry, 1979, rule A 21.1. Such numbering is illustrated in the figure in lines 22–26 on page 2 of the aforementioned WO 94/11406.

Most preferably the indenyl has 1 to 3 hydrocarbyl substitutents or one trialkylsilyl substituent, optionally with 1 or 2 hydrocarbyl substitutents, and each substituent is located at a different one of the 1, 2, or 3 positions of the indenyl. The metallocenes (1-phenyl indenyl) (cyclopentadienyl) zirconium dichloride, (1,2,3-trimethyl indenyl) (cyclopentadienyl) zirconium dichloride, (2-methyl indenyl) (cyclopentadienyl) zirconium dichloride, (1-trimethylsilyl indenyl) (cyclopentadienyl) zirconium dichloride, and (1,2-dimethyl indenyl) (cyclopentadienyl) zirconium dichloride have been found to have particularly desirable characteristics.

The inventive metallocenes can be prepared using techniques similar to those that have been used in the past for making unsymmetrical metallocenes. One example involves reacting an alkali metal salt of the indenyl compound in a suitable solvent under suitable reaction conditions with a suitable transition metal compound, for example CpMeCl$_3$, wherein M is Zr, Hf, or Ti.

An especially preferred method involves carrying out the reaction of the indenyl-containing salt and the transition metal compound in the presence of a liquid diluent which is non-halogenated and non-coordinating toward the transition metal compound. Examples of such suitable liquid include hydrocarbons such as toluene, pentane, or hexane as well as non-cyclic ether compounds such as diethylether. It has been found that the use of such non-halogenated non-coordinating solvents generally allows one to obtain large amounts of substantially pure metallocenes in a more stable form, and often allows the reaction to be conducted under higher temperature conditions, than when dichloromethane is used as the diluent.

The formation of the alkali metal salt of the indenyl compound can be formed using generally any technique known in the art. For example, such can be prepared by reacting an alkali metal alkyl with the substituted indene. The molar ratio of the alkali metal alkyl to the indene can vary; generally however, the ratio would be in the range of about 0.5/1 to about 1.5/1, still more preferably about 1/1.

Typically, the alkali metal of the alkali metal alkyl would be selected from sodium, potassium, and lithium, and the alkyl group would have 1 to 8 carbon atoms, more preferably 1 to 4 carbon atoms. In the preferred embodiment if the indenyl salt is formed using tetrahydrofuran (THF) as the liquid solvent, the salt is isolated and substantially all of the THF is removed before the salt is contacted with the transition metal halide. The molar ratio of the indenyl salt to the transition metal compound can vary over a wide range depending upon the results desired. Typically, however, the indenyl salt is used at a molar ratio of the indenyl compound to the transition metal compound, i.e. CpMCl$_3$, of about 1 to 1.

The resulting metallocene can be recovered and purified using conventional techniques known in the art such as filtration, extraction, crystallization, and recrystallization. It is generally desirable to recover the metallocene in a form that is free of any substantial amount of by-product impurities. Accordingly, recrystallization and fractional crystallization to obtain relatively pure metallocenes is desirable. Dichloromethane has been found to be particularly useful for such recrystallizations. Since the stability of the various metallocenes varies, it is generally desirable to use the metallocenes soon after their preparation or at least to store the metallocene under conditions favoring their stability. For example the metallocenes can generally be stored in the dark at low temperature, i.e. below 0° C., in the absence of oxygen and water.

The resulting inventive indenyl-containing metallocenes can be used in combination with a suitable cocatalyst for the polymerization of olefinic monomers. In such processes the metallocene or the cocatalyst can be employed on a solid insoluble particulate support.

Examples of suitable cocatalysts include generally any of those cocatalysts which have in the past been employed in conjunction with transition metal containing metallocene olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, triisobutyl aluminum, diethyl aluminum chloride, diethyl aluminum hydride, and the like.

The currently most preferred cocatalyst is an aluminoxane. Such compounds include those compounds having repeating units of the formula

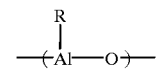

where R is an alkyl group generally having 1 to 5 carbon atoms.

Aluminoxanes, also sometimes referred to as poly (hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561. The currently preferred cocatalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096.

The indenyl-containing metallocenes in combination with the aluminoxane cocatalyst can be used to polymerize olefins, especially alpha olefins having 2 to 12 carbon atoms. Often such polymerizations would be carried out in a homogeneous system in which the catalyst and cocatalyst were soluble; however, it is within the scope of the present invention to carry out the polymerizations in the presence of supported or insoluble particulate forms of the catalyst and/or cocatalyst. The catalyst is thus considered suitable for solution, slurry, or gas phase polymerization. It is within the scope of the invention to use a mixture of two or more of the inventive indenyl-containing metallocenes or a mixture of an inventive indenyl-containing metallocene with one or more other cyclopentadienyl-type metallocenes.

The indenyl-containing metallocenes when used with aluminoxane are particularly useful for the polymerization of ethylene in the presence or absence of other olefins. Examples of other olefins that might be present include mono-unsaturated aliphatic alpha-olefins having 3 to 10 carbon atoms. Examples of such olefins include propylene, butene-1, pentene-1,3-methylbutene-1, hexene-1,4-methylpentene-1,3-methylpentene-1, heptene-1, octene-1, decene-1, 4,4-dimethyl-1-pentene, 4,4-diethyl-1-hexene, 3-4-dimethyl-1-hexene, and the like and mixtures thereof.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914. It is considered that generally any of the polymerization procedures used in the prior art with any transition metal based catalyst systems can be employed with the present inventive indenyl-containing metallocenes.

The amount of cocatalyst can vary over a wide range. It is currently preferred for the molar ratio of the aluminum in the aluminoxane to the transition metal in the metallocene to be in the range of about 0.1:1 to about 100,000:1 and more preferably about 5:1 to about 15,000:1. In many cases, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about −60° C. to about 300° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer.

Various techniques can be used for preparing the substituted indenes needed for producing the metallocenes of the present invention. Monoalkyl substituted indenes can be produced by alkylation of indenyl lithium. It has been discovered that less of the disubstitution products are obtained if the alkylation is conducted using diethyl ether as a reaction medium rather than THF. The 1-phenyl indenyl can be produced by reacting 1-indanone with phenylmagnesium bromide and then dehydrating the resulting 1-phenyl-1-indanone. This is preferably conducted in the presence of p-toluenesulfonic acid in toluene. An analogous procedure can be used to produce alkyl and aryl 2-substituted indenes. For example, a Grignard reaction of 2-indanon can be conducted using the respective alkyl or aryl halide. Multiple alkyl or aryl substituted indenes can be produced through reaction of the respective substituted 1-indanone with the appropriate Grignard reagent followed by dehydration of the produced indanol. For example 2,3-dimethyl-1-indanone or 3-methyl indanone can be reacted with methyl magnesium iodide to yield the respective methyl substituted indanol which is dehydrated to 1,2,3-trimethylindene or 1,3-dimethyl indene, respectively. In the latter case a mixture of p-tosyl chloride and pyridine is preferably used to effect the dehydration of the hydroxy group. The reduction of 2,3-dimethyl- 1-indanone with lithium aluminum hydride and further elimination of water with p-toluenesulfonic acid leads to 1,2-dimethylindene. The compound 3-phenyl-1-methyl indene can be prepared by reacting 3,3-diphenylpropionic acid with aluminum trichloride in dichloromethane to obtain 3-phenyl-1-indanone which in turn is reacted with methyl magnesium iodide to produce the indanol which was then dehydrated with p-toluenesulfonic acid. A similar technique can be used to prepare 1-phenyl-3-phenyl indene by substituting phenyl magnesium bromide for the methyl Grignard reagent. Trimethylsilyl substituted indenes can be obtained by reacting the lithium salt of a substituted or unsubstituted indene with trimethylchlorosilane. Preferably this is done in diethyl ether. Such a technique has been used to produce 1-trimethylsilyl-3-methyl indene, 1-trimethylsilyl-3-phenyl indene, 1,3-di-trimethylsilyl indene, 1-trimethylsilyl-2-methyl indene, 1-trimethyl-2-phenyl indene, and 1-trimethylsilyl-1-methyl-2-methyl-3-methyl indene.

A further understanding of the present invention, its various aspects, objects and advantages will be provided by the following examples.

In the following examples, the metallocene preparations were carried out routinely using the Schlenk technique, with strict exclusion of air and moisture, by means of purified and dried inert gas.

The solvents which were used were dried over a sodium/potassium alloy or over phosphorus pentoxide in the case of dichloromethane and distilled in circulation equipment under an inert atmosphere. Toluene was additionally distilled over phosphorus pentoxide and dichloromethane was distilled over calcium hydride. Deuterated solvents for the NMR spectroscopy were stored over a molecular sieve.

The melting points of the organic compounds were determined in open tubes and those of the organometallic compounds were determined in closed tubes under nitrogen.

The organic compounds were characterized using a gas chromatograph with flame ionization detector and a fused silica column with helium as the carrier gas. The mass spectra were carried out using a mass spectrometer with electron impact ionization energy of 70 eV. The samples were introduced with the help of a direct inlet system, or they were injected in the form of solutions.

The thermal properties of the produced polymers was evaluated using a Differential Scanning Calorimetry Device, a DSC 7 model obtained from Perkin Elmer. The polymer samples were dried under vacuum prior to the measurements. The technique involved fusing 5 to 10 gram samples in standard aluminum pans, first by heating at 20 degrees K/min from −40° C. to 200° C., holding at 200° C. for 3 minutes, and then cooling at 20 degrees K/min to −40° C. A second heating phase like the first heating phase was then conducted. The melting points and enthalpies of fusion were measured during the second heating phase. The temperature was linearly corrected using indium as a standard (melting point 429.78 K and enthalpy of fusion 28.45 J/g).

The molecular weight of the polymers were determined using an Ubbelohde capillary viscometer in cis/tran-decalin at 135+/−0.1° C. The samples were dried under vacuum prior to the measurement and then weighed out into small flasks that could be sealed. The polymers were then dissolved in a precisely measured quantity of the decalin within three or for hours at 140° to 105° C. Any insoluble material was filtered out using glass wool. Calibration curves for three different polymer concentrations were evaluated for the determination of the viscosity average molecular weight, i.e. M$\eta$.

EXAMPLE I

Unbridged metallocenes were prepared by dissolving about 2.4 mmol of the selected indenyl compound in diethyl ether and then mixing with about 1.5 ml of a 1.6 M hexane solution of n-butyl lithium. After stirring for about three hours at room temperature an equimolar quantity of a cyclopentadienyl trichloride metallocene was added and the mixture stirred for about four more hours at room temperature. The liquid was evaporated using a vacuum. The residue was extracted with toluene and the suspension was filtered over sodium sulfate. The resulting filtrate was concentrated by evaporation and brought to the point of crystallization by cooling to −78° C.

EXAMPLE II

Various unbridged metallocenes prepared as described in Example I were then evaluated for their effectiveness in the polymerization of ethylene. The technique involved combining about 1 to 5 mg of the metallocene with 1 to 5 ml of a 30 weight percent toluene solution of commercial methyluminoxane. The resulting solution was further diluted with additional toluene so as to result in a solution containing about 1 to 5 mg of the metallocene in about 20 ml of the solution. The resulting mixture was used as the catalyst system within about 30 minutes of its preparation.

The polymerizations were conducted in a 1 liter autoclave. First 500 ml of pentane was mixed with 1 ml of the commercial methylaluminoxane and stirred for 15 min at 30° C. Then the catalyst system solution was added. The autoclave was thermostatically regulated at 60° C. and ethylene was supplied at a pressure of 10 bar. After a reaction time of one hour, the pressure was released and the polymer dried under a vacuum.

Some comparable control runs were carried out using prior art unbridged metallocenes such as bis cyclopentadienyl, bis indenyl, and 1-methyl indenyl pentamethylcyclopentadienyl metallocenes. Also a new metallocene (1-phenyl indenyl) indenyl zirconium dichloride was evaluated.

The activities observed with the various unbridged metallocenes and some of the properties of the resulting polymers are compared in the following tables. Note that in a few cases noted in the table the polymerization was ted at 30° C. rather than 60° C.

TABLE 1

| Run No. | Complex | Activity [g PE (mmol M-h)] | $M_\eta$ [$10^3$ g/mol] | DSC $T_m[°C.]$ $\Delta H_m[J/g]$, $\alpha[\%]$ |
|---|---|---|---|---|
| 1 | (1-Me-In)CpZrCl$_2$ | 530,000 | 380 | 140.2 151.7, 52 |
| 2 | (1-MeO(CH$_2$)$_2$-In)CpZrCl$_2$ | 4,500* | 560 | 143.7 105.0, 36 |
| 3 | (1-Me$_3$Si-In)CpZrCl$_2$ | 320,000 | 950 | 142.8 149.0, 51 |
| 4 | (1-Ph-In)CpZrCl$_2$ | 1,400,000 | 580 | 143.8 161.2, 55 |
| 5 | (2-Me-In)CpZrCl$_2$ | 320,000 | 910 | 142.5 156.0, 53 |
| 6 | (2-Ph-In)CpZrCl$_2$ | 230,000 | 520 | 144.1 148.8, 51 |
| 7 | 1,2-Me$_2$-In)CpZrCl$_2$ | 356,000 | 740 | not determined |
| 8 | (1,3-Me$_2$-In)CpZrCl$_2$ | 555,000 | 660 | 142.3 161.2, 55 |
| 9 | (1,3-Ph$_2$-In)CpZrCl$_2$ | 274,000 | 780 | 141.4 135.8, 46 |
| 10 | (1,2,3-Me$_3$-In)CpZrCl$_2$ | 1,100,000 | 600 | 140.8 169.6, 58 |
| 11 | (1-Me-In)(Me$_3$Si-Cp)ZrCl$_2$ | 121,000 | 660 | 141.8 160.5, 55 |
| 12 | Cp$_2$ZrCl$_2$ | 136,000 | 290 | 142.4 160.0, 55 |
| 13 | Ind$_2$ZrCl$_2$ | 293,000 | 470 | 143.5 168.2, 57 |
| 14 | (1-MeIn)Cp*ZrCl$_2$ | 154,000 | 540 | 146.9 123.7, 42 |
| 15 | (1-Ph-In)InZrCl$_2$ | 50,000 | 320 | 143.4 175.1, 60 |

*Polymerization temperature 30° C.

The data shows that the inventive metallocenes were more active than the either the bis (cyclopentadienyl) zirconium dichloride or the (1-methylindenyl) (pentamethylcyclopentadienyl) zirconium dichloride and a number were even more active than the bis (indenyl) zirconium dichloride. The catalysts with the highest activities were the (1-phenyl indenyl) (cyclopentadienyl) zirconium dichloride and the (1,2,3-trimethyl indenyl) (cyclopentadienyl) zirconium dichloride. The runs using (1-methyl indenyl) (trimethylsilylcyclopentadienyl) zirconium dichloride and (1-methyl indenyl) (pentamethylcyclopentadienyl) zirconium dichloride suggest that the introduction of a substituent on the cyclopentadienyl ligand has an adverse effect upon activity. A similar result is noted when one compares the activity of (1-phenyl indenyl) (indenyl) zirconium dichloride with that of(1-phenyl indenyl) (cyclopentadienyl) zirconium dichloride.

The polymers with the highest molecular weight were produced using the inventive metallocenes having a trimethylsilyl substituent at the 1 position of the indenyl or a methyl substituent at the 2 position of the indenyl.

EXAMPLE III

Another series of polymerizations were conducted using various unbridged indenyl titanium-containing metallocenes. The conditions were as set forth in Example II. The polymerization temperature was usually 30° C. The results are set forth in the following table.

TABLE 2

| Run No. | Complex | Activity [g PE (mmol M-h)] | $M_\eta$ [$10^3$ g/mol] |
|---|---|---|---|
| 16 | (1-PhIn)CPTiCl$_2$ | 2100 | 920 |
| 17 | (2-PhIn)CpTiCl$_2$ | 1100 390* | 680 830* |
| 18 | (1,2,3-Me$_3$In)CPTiCl$_2$ | 680 | 1500 |
| 19 | (1-Me$_3$SiIn)CPTiCl$_2$ | 1700 | 1120 |
| 20 | (In)(MeCp)TiCl$_2$ | 1700 | not determined |
| 21 | (1-MeIn)(Cp)TiCl$_2$ | 900* 2200 | 195* 1625 |

*Polymerization temperature 60° C.

A comparison of the data in Table 2 with that in Table 1 demonstrates that the inventive titanium metallocenes are not as active as the inventive zirconium metallocenes however they generally produce a higher molecular weight polymer. In contrast the applicants have observed that the inventive hafnium metallocenes were found to produce lower molecular weight products than comparable inventive zirconium metallocenes.

EXAMPLE IV

A series of the inventive zirconium based metallocenes were also evaluated for their effectiveness in the polymerization of propylene. The polymerizations were also conducted in the one liter autoclave using catalyst system solutions prepared as described in Example II. In the polymerizations about 500 ml of propylene was condensed in the autoclave and stirred with about 5 ml of the commercial 30 weight percent toluene solution of methylaluminoxane. 5 The catalyst solution was added by means of a pressure burette. The autoclave was thermostatically regulated at 0° C. and the reaction mixture stirred for one hour. Then the pressure was released and the polymer dried under a vacuum. The results are summarized in the following table.

TABLE 3

| Run No. | Complex | Activity [g PP/ (mmol/ M · h)] | $M_\eta$ [g/mol] | GPC $M_n$ [g/mol] $M_w$ [g/mol] $M_w/M_w$ | DSC $T_g[°C.]$ $T_m[°C.]$ $\Delta H_{m[J/g]}$ | $^1$C-NMR [%] |
|---|---|---|---|---|---|---|
| 22 | (1-PhIn)CpZrCl$_2$ | 800 | 75,000 | 30,500 80,000 2.6 | −11.0 157.2 15.0 | 6.9 (rrrr) 7.9 (mmmm) |

TABLE 3-continued

| Run No. | Complex | Activity [g PP/ (mmol/ M·h)] | $M_\eta$ [g/mol] | GPC $M_n$ [g/mol] $M_w$ [g/mol] $M_w/M_n$ | DSC $T_g[°C.]$ $T_m[°C.]$ $\Delta H_{m[J/g]}$ | $^{13}$C-NMR [%] |
|---|---|---|---|---|---|---|
| 23 | (2-MeIn) CpZrCl$_2$ | 4,100 | 390,000 | 73,100 372,000 5. | −9.6 159.4 0.4 | 9.7 (mmmm) |
| 24 | (2-PhIn) CpZrCl$_2$ | 1,700 | 260,000 | 87,200 282,000 3.2 | −10.6 142.4 3.2 | 7.2 (mmmm) |
| 25 | (1,3-Ph$_2$ In)CpZr Cl$_2$ | 700 | 160,000 | 45,800 147,900 3.2 | −10.3 155.3 8.6 | 10.7 (rrrr) |

The table shows that the inventive metallocenes can be used to polymerize propylene. The activity and the molecular weight of the produced polymer vary depending upon the type and position of the substituents. The relatively high melting temperatures and the low tacticity may be due to block like polymer structures. The polymer produced with (2-methylindenyl) (cyclopentadienyl) zirconium dichloride possesses an unusually broad $M_w/M_n$ for a metallocene and a melting enthalpy of 0.5 J/g. This implies low crystalline percentage despite an isotactic content of 9.7%. In contrast the polymer produced with (2-phenylindenyl) cyclopentadienyl zirconium dichloride shows lower isotacticity, narrower molecular weight distribution, and a higher melting enthalpy. The metallocene of Run 25 produces a polymer having almost twice the molecular weight of the polymer produced the metallocene used in Run 22.

That which is claimed is:

1. A catalyst system useful for the polymerization of olefins comprising the combination of an unbridged metallocene of the formula (In)(Cp)MQ$_2$ wherein In is a substituted indenyl radical having a substituent in at least one of the 1, 2, or 3 positions, said substituents being selected from phenyl radicals, alkyl radicals having 1 to 10 carbon atoms and trialkylsilyl radicals wherein the alkyl groups have 1 to 4 carbons; Cp is an unsubstituted cyclopentadienyl radical; M is a transition metal selected from the group consisting of titanium, zirconium, and hafnium; and each Q is the same or different and is selected from the group consisting of hydrocarbyl radicals having 1 to 12 carbon atoms, alkoxy radicals having 1 to 12 carbon atoms, aryloxy radicals having 6 to 12 carbon atoms, hydrogen, and halides and a suitable cocatalyst.

2. A catalyst system according to claim 1 wherein the cocatalyst is selected from organoaluminum compounds.

3. A catalyst system according to claim 2 wherein methylaluminoxane is employed as cocatalyst.

4. A catalyst system according to claim 3 wherein M of the metallocene is zirconium and each Q is chloride.

5. A catalyst system according to claim 4 wherein the metallocene is selected from the group consisting of (1-phenyl indenyl) (cyclopentadienyl) zirconium dichloride, (1,2,3-trimethyl indenyl) (cyclopentadienyl) zirconium dichloride, (2-methyl indenyl) (cyclopentadienyl) zirconium dichloride, (1-trimethylsilyl indenyl) (cyclopentadienyl) zirconium dichloride, and (1,2-dimethyl indenyl) (cyclopentadienyl) zirconium dichloride.

6. A process for preparing a polymer comprising contacting at least one olefin under suitable reaction conditions with a catalyst system produced by combining an unbridged metallocene of the formula (In)(Cp)MQ$_2$ wherein In is a substituted indenyl radical having a substituent in at least one of the 1, 2, or 3 positions, said substituents being selected from phenyl radicals, alkyl radicals having 1 to 10 carbon atoms and trialkylsilyl radicals wherein the alkyl groups have 1 to 4 carbons; Cp is an unsubstituted cyclopentadienyl radical; M is a transition metal selected from the group consisting of titanium, zirconium, and hafnium; and each Q is the same or different and is selected from the group consisting of hydrocarbyl radicals having 1 to 12 carbon atoms, alkoxy radicals having 1 to 12 carbon atoms, aryloxy radicals having 6 to 12 carbon atoms, hydrogen, and halides; and a suitable cocatalyst.

7. A process according to claim 6 wherein the cocatalyst of the catalyst system comprises an organoaluminum compound.

8. A process according to claim 7 wherein an organoaluminoxane cocatalyst having repeating units of the formula

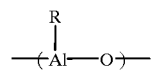

wherein each R is an alkyl radical having 1 to 5 carbon atoms is employed.

9. A process according to claim 8 wherein the metallocene of the catalyst system is selected from the group consisting of (1-phenyl indenyl) (cyclopentadienyl) zirconium dichchloride, (1,2,3-trimethyl indenyl) (cyclopentadienyl) zirconium dichloride, (2-methyl indenyl) (cyclopentadienyl) zirconium dichloride, (1-trimethyl indenyl) (cyclopentadienyl) zirconium dichloride, and (1,2-dimethyl indenyl) (cyclopentadienyl) zirconium dichloride.

10. A process according to claim 8 wherein ethylene is polymerized.

11. A process according to claim 8 wherein propylene is polymerized.

12. A process according to claim 10 wherein the polymerization is conducted under particle form polymerization conditions.

13. A process according to claim 12 wherein said polymerization is conducted in a continuous loop reactor.

14. A process according to claim 10 wherein said catalyst system is prepared by combining (1-phenylindenyl) cyclopentadienyl zirconium dichloride and the cocatalyst.

15. A process according to claim 10 wherein said catalyst system is prepared by combining (1,2,3-trimethylindenyl) cyclopentadienyl zirconium dichloride and the cocatalyst.

16. A process according to claim 10 wherein said catalyst system is produced using a metallocene of the formula (In)(Cp)ZrCl$_2$ wherein Cp is an unsubstituted cyclopentadienyl radical, In is a substituted indenyl radical wherein each substituent is a methyl radical and is located in at least one of the 1, 2, and 3 positions.

17. A process according to claim 16 wherein said catalyst system is produced using (1,3-dimethyl indenyl) (cyclopentadienyl) zirconium dichloride.

18. A process according to claim 16 wherein said catalyst system is produced using (1-methyl indenyl) (cyclopentadienyl) zirconium dichloride.

19. A process according to claim 16 wherein said catalyst system is produced using (2-methyl indenyl) (cyclopentadienyl) zirconium dichloride.

* * * * *

UNITED STATES PATENT AND TRADEMARK OFFICE
CERTIFICATE OF CORRECTION

PATENT NO.   : 6,037,427

DATED        : March 14, 2000

INVENTOR(S)  : Claudia Schmid et al

It is certified that error appears in the above-identified patent and that said Letters Patent is hereby corrected as shown below:

Claim 1, line 46, after "halides", please insert — ; —.

Claim 9, line 31, after "dichloride", delete "(1-trimethyl indenyl)" and insert therefor — (1-trimethylsilyl indenyl) —.

Signed and Sealed this

Thirteenth Day of February, 2001

Attest:

NICHOLAS P. GODICI

Attesting Officer    Acting Director of the United States Patent and Trademark Office